United States Patent
Cheng et al.

(10) Patent No.: US 12,031,185 B2
(45) Date of Patent: Jul. 9, 2024

(54) MOLECULAR BEACON DELIVERY SYSTEM FOR DIRECTLY DETECTING CIRCULATING TUMOR CELLS IN BLOOD, METHOD OF PREPARING THE SYSTEM AND METHOD OF USING THE SYSTEM

(71) Applicant: Wuhan University, Wuhan (CN)

(72) Inventors: Sixue Cheng, Wuhan (CN); Chang Xu, Wuhan (CN)

(73) Assignee: WUHAN UNIVERSITY, Wuhan (CN)

( * ) Notice: Subject to any disclaimer, the term of this patent is extended or adjusted under 35 U.S.C. 154(b) by 233 days.

(21) Appl. No.: 17/405,004

(22) Filed: Aug. 17, 2021

(65) Prior Publication Data

US 2022/0064739 A1   Mar. 3, 2022

(30) Foreign Application Priority Data

Aug. 27, 2020 (CN) .......................... 202010891737.2

(51) Int. Cl.
  *C12Q 1/6886* (2018.01)

(52) U.S. Cl.
  CPC ...... *C12Q 1/6886* (2013.01); *C12Q 2600/118* (2013.01); *C12Q 2600/158* (2013.01); *C12Q 2600/178* (2013.01)

(58) Field of Classification Search
  None
  See application file for complete search history.

(56) References Cited

PUBLICATIONS

Pu et al (A Practical Method for Functionalized Peptide or Amide Bond Formation in Aqueous-Ethanol Media with EDC as Activator, Org. Process Res. Dev. 2009, 13, 2, 310-314) (Year: 2009).*

De Santiago et al (On high purity fullerenol obtained by combined dialysis and freeze-drying method with its morphostructural transition and photoluminescence, Separation and Purification Technology, vol. 210, 2019) (Year: 2019).*

Min Shin et al (A PEGylated hyaluronic acid conjugate for targeted cancer immunotherapy, Journal of Controlled Release, vol. 267, pp. 181-190, Dec. 2017), (Year: 2017).*

Liu et al (A Dual-Targeting Delivery System for Effective Genome Editing and In Situ Detecting Related Protein Expression in Edited Cells, Biomacromolecules 2018, 19, 7, 2957-2968), (Year: 2018).*

* cited by examiner

*Primary Examiner* — Laura B Goddard
*Assistant Examiner* — Sarah A Alsomairy
(74) *Attorney, Agent, or Firm* — JCIP GLOBAL INC.

(57) ABSTRACT

A molecular beacon delivery system for directly detecting circulating tumor cells in blood, comprising nanoparticles self-assembled by a polymer material, protamine, and a molecular beacon.

3 Claims, 6 Drawing Sheets

MOLECULAR BEACON DELIVERY SYSTEM FOR DIRECTLY DETECTING CIRCULATING TUMOR CELLS IN BLOOD, METHOD OF PREPARING THE SYSTEM AND METHOD OF USING THE SYSTEM

CROSS-REFERENCE TO RELATED APPLICATIONS

Pursuant to 35 U.S.C. § 119 and the Paris Convention Treaty, this application claims foreign priority to Chinese Patent Application No. 202010891737.2 filed Aug. 27, 2020, the contents of which, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to the field of biomedicine, and more particularly to a molecular beacon delivery system for directly detecting circulating tumor cells in blood, and a preparation method and use thereof.

At present, with the impact of many factors of people's lifestyle and living environment and population aging, prevention and treatment of cancer have become a major issue of public health in China. According to the latest data from the World Health Organization, about ⅙ of people worldwide die of cancer. Although malignant tumors greatly threaten lives and health of people, early diagnosis and optimal treatment can greatly improve survival rates of cancer patients. Conventional clinical diagnosis methods mainly include a tissue biopsy and imaging. The tissue biopsy is to take tissue from a lesion site by invasive puncture or surgery to determine a tumor type. This method not only causes invasive damage to a patient, but also causes false positive or false negative results due to hysteresis of tumor markers. The size of a tumor that can be detected by imaging is only 100 million cells (about 1 cm$^3$) or more, but the tumor has begun to metastasize when the volume is less than 1 million cells (about 0.01 cm$^3$). Therefore, as an alternative and complementary technology to the conventional detection methods, liquid biopsy appears in people's field of vision.

As a new non-invasive detection method, liquid biopsy mainly detects circulating tumor cells (CTCs), circulating tumor DNA, and exosomes that shed into body fluids from solid tumors, so as to carry out early screening and diagnosis, targeted medication guidance, dynamic monitoring of curative effects, and real-time prognostic evaluation for patients. Due to the characteristics of diverse sampling sites and detection repeatability, the liquid biopsy has great potential value in precise treatment. The CTCs refer to various tumor cells from peripheral blood. These cells shed from a primary tumor, and are carried by the blood or lymphatic system around the body, to find new metastases in the body, resulting in progression of disease. Compared with the circulating tumor DNA and the exosomes, the CTCs can better reflect the progression of disease because the CTCs include all genetic information of the primary tumor site. However, the quantity of the CTCs in the blood is relatively extremely small, and only 0-100 CTCs are found in every $10^6$-$10^7$ white blood cells in 1 mL of peripheral blood. Therefore, it is particularly important to develop an efficient detection technology for the CTCs.

The detection of the CTCs in the blood mainly has two steps: cell enrichment and downstream characterization. The cell enrichment is mainly a series of technical methods such as a density gradient centrifugation method, a membrane filtration separation method, a magnetic-activated cell sorting method, and a polypeptide nanomagnetic bead method developed based on physical characteristics (density, size, and the like), surface antigens, and surface affinity of the CTCs. Means of the downstream characterization mainly include RT-PCR, laser scanning, flow cytometry, immunocytochemistry, single cell sequencing, and the like. Main defects of this detection method of enrichment before characterization are as follows: 1. the CTCs are easily damaged during the enrichment; 2. living cells cannot be detected in real time; and 3. determination of the cells after the enrichment is overly dependent on various staining methods, leading to a cumbersome process, and in addition, a determination result is prone to be false negative due to the lack of surface antigens. Therefore, it is particularly important to develop a nanomaterial that can first detect the CTCs in the blood and then enrich the CTCs. Most of the reported similar nanomaterials are composed of metal or inorganic non-metal materials, which have poor biocompatibility. Moreover, protein molecules on the surface of the CTCs can only be detected through antibodies or aptamers, and nucleic acid molecules inside the cells cannot be detected. Therefore, it is extremely urgent to develop a nanomaterial with good biocompatibility and real-time reflection of nucleic acid expression inside cells.

SUMMARY

A first objective of the disclosure is to provide a molecular beacon delivery system for directly detecting circulating tumor cells in blood, which can efficiently target circulating tumor cells in a blood environment to efficiently detect the circulating tumor cells.

A second objective of the disclosure is to provide a preparation method of the molecular beacon delivery system for directly detecting circulating tumor cells in blood, which has a simple preparation process and is easy to be adjusted.

A third objective of the disclosure is to provide use of the molecular beacon delivery system for directly detecting circulating tumor cells in blood.

A solution used to achieve the first objective of the disclosure is as follows: a molecular beacon delivery system for directly detecting circulating tumor cells in blood is nanoparticles self-assembled by a polymer material, protamine, and a molecular beacon.

When a target is not met, the molecular beacon in the molecular beacon delivery system nanoparticles of the disclosure is in a state of fluorescence quenching through fluorescence resonance energy transfer. Aptamers on the surface of the nanoparticles can bind with protein overexpressed on the surface of the circulating tumor cells. The nanoparticles enter the cells through active targeting endocytosis, disintegrate in the acidic environment of lysosome in the circulating tumor cells, and then release the molecular beacon into the cytoplasm. The specific nucleic acid in the cytoplasm binds with the molecular beacon, thereby initiating fluorescence recovery of the molecular beacon. The change of nucleic acid levels in the tumor cells can be monitored in real time through the fluorescence intensity. The cells in the blood of cancer patients are mainly composed of blood cells and circulating tumor cells. Because red blood cells and platelets have no endocytosis capacity, the nanoparticles do not enter the red blood cells and the platelets. There is no protein that can be specifically recognized by the nanoparticles on the surface of white blood cells, so that the nanoparticles do not enter the white blood cells either. Therefore, the nanoparticles can efficiently detect the circulating tumor cells in the blood.

The polymer material comprises any one of aptamer-functionalized hyaluronic acid, polypeptide-functionalized hyaluronic acid, aptamer-functionalized carboxymethyl chitosan, polypeptide-functionalized carboxymethyl chitosan, aptamer-functionalized sodium alginate, polypeptide-functionalized sodium alginate, aptamer-functionalized heparin sodium, and polypeptide-functionalized heparin sodium, or comprises any one of hyaluronic acid, carboxymethyl chitosan, sodium alginate, and heparin sodium.

The molecular beacon comprises any one of a common molecular beacon, a locked molecular beacon, a stemless molecular beacon, a fluorescence transfer molecular beacon, catalyzed hairpin assembly (CHA), and hybridization chain reaction (HCR). CHA is a catalyzed hairpin assembly DNA reaction. HCR is a hybridization chain reaction.

For the molecular beacon, the 5' end is marked with a fluorophore, and the 3' end is marked with a fluorescence quencher.

The fluorescence emitted by the fluorophore in the molecular beacon can be quenched by the quencher. When the molecular beacon binds with target cells, a stem-loop of the molecular beacon is opened, and the fluorophore is far away from the quencher, so that a fluorescent signal can be detected.

Nucleic acid detected by the molecular beacon delivery system comprises any one of survivin mRNA, p53 mRNA, EpCAM mRNA, RPL15 mRNA, miR-21, and miR-205.

A detected sample comes from a single-stranded DNA or RNA sample, a cell sample, or a blood sample paired with nucleic acid.

A solution used to achieve the second objective of the disclosure is as follows: a preparation method of the molecular beacon delivery system for directly detecting circulating tumor cells in blood includes the following steps:
(1) aptamer-functionalizing or polypeptide-functionalizing the polymer material to obtain a functionalized polymer material;
(2) adding deionized water to a protamine solution to form a solution A, adding deionized water to a molecular beacon solution to form a solution B, and dropwise adding the solution A to the solution B and mixing evenly; and
(3) adding the functionalized polymer material obtained in (1) to the mixed solution obtained in (2), and continually mixing evenly, to obtain the molecular beacon delivery system.

Synthesis of Functionalized Biopolymer Material/Protamine/Molecular Beacon Nanoparticles Synthesis principle: A nanosystem is synthesized by a self-assembly method. The positively charged protamine sulfate (PS) and the negatively charged molecular beacon (MB) form protamine/molecular beacon nanoparticles through electrostatic interaction, and then a negatively charged functionalized polymer material is added to the protamine/molecular beacon nanoparticles positively charged on the surface, to prepare the functionalized biopolymer material/protamine/molecular beacon nanoparticles.

A specific step of the step (1) is any one of I or II:
I. dissolving the polymer material in a PBS buffer solution, adding a catalyst EDC/HoBt for activation at 25° C., and then adding aminated aptamer or polypeptide and reacting at 25° C.; and placing the product obtained after an amidation reaction in a dialysis bag for dialysis, and freeze-drying the dialyzed product, to obtain the functionalized polymer material; or
II. dissolving aptamer or polypeptide in a PBS buffer solution, adding a catalyst EDC/HoBt for activation at 25° C., and then adding the polymer material and reacting at 25° C.; and placing the product obtained after an amidation reaction in a dialysis bag for dialysis, and freeze-drying the dialyzed product, to obtain the functionalized polymer material.

When the polymer material is hyaluronic acid, sodium alginate, or heparin sodium, the functionalized polymer material is prepared by the method I. When the polymer material is carboxymethyl chitosan, the functionalized polymer material is prepared by the method II.

In the steps I and II, after the catalyst EDC/HoBt is added, the molar ratio of —COOH to EDC to HoBt in the solution is 1:1.2:1.2, and the molar ratio of the polymer material to the aptamer or the polypeptide is 10:1.

In (3), after the functionalized polymer material is added, the mass ratio of the protamine to the molecular beacon to the functionalized polymer material in the mixed solution is 30:1-2:5-15, and the concentration of the protamine is 0.3 µg/µL.

A solution used to achieve the third objective of the disclosure is as follows: use of the molecular beacon delivery system for directly detecting circulating tumor cells in blood is provided, and the molecular beacon delivery system for directly detecting circulating tumor cells in blood is used in the detection field of cervical cancer, breast cancer, prostate cancer, melanoma, non-small cell lung cancer, and liver cancer.

The disclosure has the following advantages and beneficial effects:

All materials of the molecular beacon delivery system of the disclosure are biocompatible materials, and direct incubation in the blood does not cause toxic side effects of blood cells and circulating tumor cells. The particle size, potential, and surface morphology of the nanoparticles of the molecular beacon delivery system of the disclosure can meet the requirements for cell entry, and the nanoparticles have good stability and biocompatibility.

The preparation principle of the molecular beacon delivery system of the disclosure pertains to electrostatic interaction, and all processes are carried out in the aqueous phase. The preparation process is simple and efficient, and the nanoparticles can be synthesized in only half an hour. Different targeting aptamer and polypeptide molecules can be bound to polymer chains on the surface of the synthesized nanoparticles, so that the nanoparticles can reach tumor cell sites efficiently in a complex blood environment. The nanomaterial can encapsulate the molecular beacon inside to protect the beacon from interference of enzyme, protein, and other molecules in the blood. In addition, after the nanoparticles enter the circulating tumor cells, in the acidic environment of lysosome, the molecular beacon is efficiently released into the cytoplasm, efficiently binding the beacon and targeted nucleic acid molecules. The nanomaterial can encapsulate the molecular beacon inside to protect the beacon from interference of enzyme, protein, and other molecules in the blood. In addition, after the nanoparticles enter the circulating tumor cells, in the acidic environment of lysosome, the molecular beacon is efficiently released into the cytoplasm, efficiently binding the beacon and targeted nucleic acid molecules.

For the preparation method of the disclosure, the synthesis process is non-toxic, simple, and rapid, is wholly carried out in the aqueous phase, and can achieve mass production.

The molecular beacon delivery system of the disclosure can be directly incubated in the blood of cancer patients, and can detect different nucleic acid molecules inside tumor cells in real time in a state of living cells, thereby avoiding damage to the cells caused by cell enrichment first. The method is further adapted to a standard method procedure of circulating tumor cells. When circulating tumor cells in the blood are detected by using the molecular beacon delivery system of the disclosure, the circulating tumor cells do not need to be enriched first, nanoparticles can be directly incubated in the blood and detect nucleic acid molecules in living cells, and fluorescence can exist in the entire circulatory system. The molecular beacon delivery system can be used in early detection, medication guidance, and metastasis monitoring of cancer, and especially in detection of cervical cancer, breast cancer, prostate cancer, melanoma, non-small cell lung cancer, and liver cancer that are at an early stage.

DETAILED DESCRIPTION

To better understand the disclosure, the following examples are further descriptions of the disclosure, but the content of the disclosure is not merely limited to the following examples.

Unless otherwise specified, the technical means used in the examples are conventional means well known to a person skilled in the art, and the raw materials used are all commercially available products.

Example 1

Synthesis and Use of Molecular Beacon Delivery System Nanoparticles

1. Synthesis of Molecular Beacon Delivery System Nanoparticles

The specific process is as follows: sodium hyaluronate or sodium alginate or heparin sodium (150 µg) was dissolved in a PBS buffer solution (pH=6.0, 1 mL), the mixed solution was activated with a catalyst EDC/HoBt (with a molar ratio of —COOH:EDC:HoBt=1:1.2:1.2) at room temperature for 1 h, and then aminated aptamer or polypeptide (150 µg) was added to react at room temperature for 24 h. Alternatively, carboxylated aptamer or polypeptide (150 µg) was activated with the catalyst EDC/HoBt at room temperature for 1 h, and then carboxymethyl chitosan (150 µg) was added to react at room temperature for 24 h. The product obtained after the reaction of the four polymer materials was placed in a dialysis bag (MWCO 10000) to be dialyzed with ultrapure water for 3 days, and the dialyzed product was freeze-dried, to finally obtain a functionalized polymer material.

Figure 1:
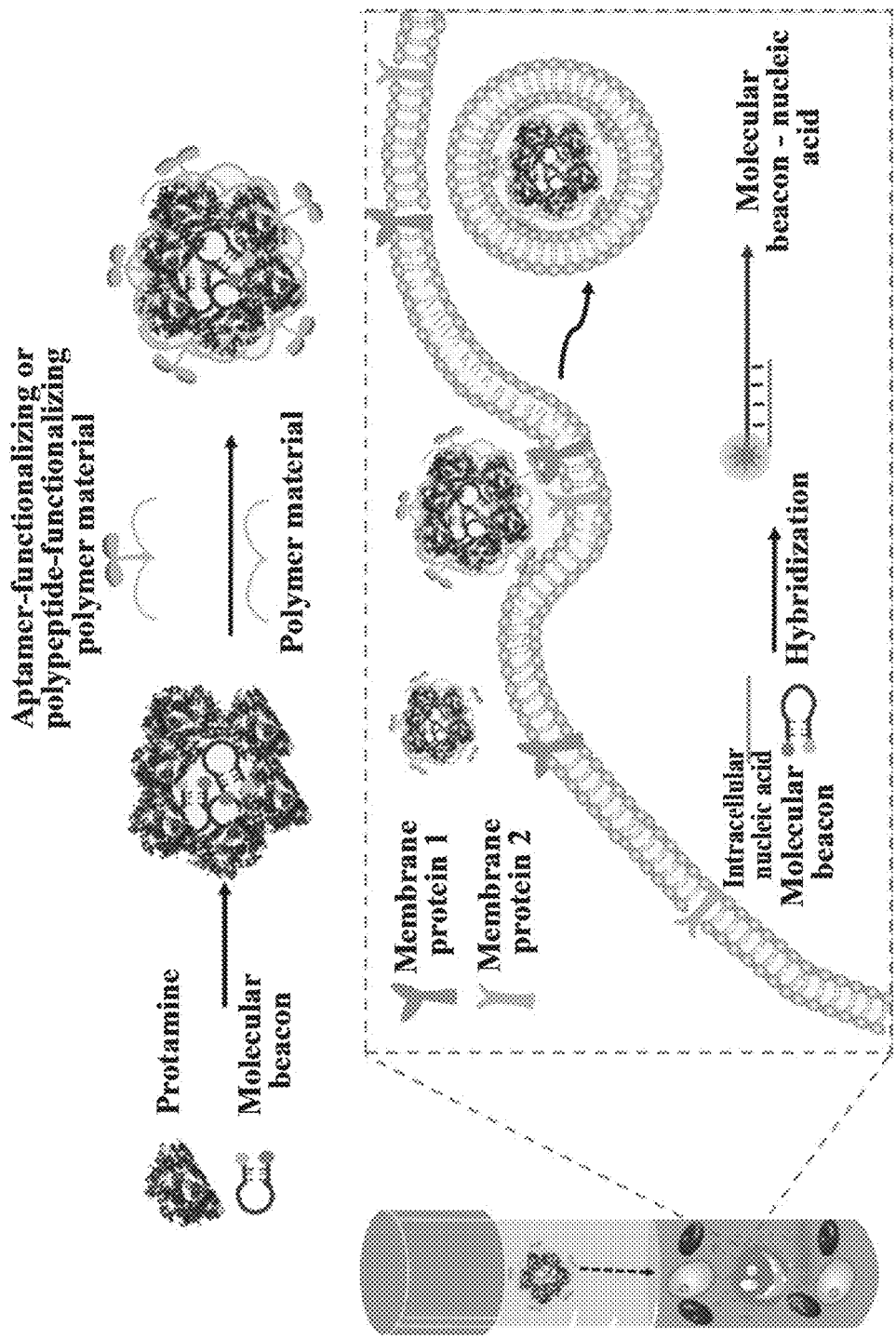
FIG. 1 is a diagram of a synthesis and action principle of a molecular beacon delivery system according to the disclosure.

Reagents used to prepare the nanoparticles were respectively dissolved in deionized water to obtain solutions with specific concentrations. A protamine solution (2 µg/µL, 15 µL) was mixed with deionized water (35 µL) to obtain a solution A with a total volume of 50 µL. A molecular beacon solution (100 nM) was mixed with deionized water (40 µL) to obtain a solution B with a total volume of 50 µL. The solution A was dropwise added to the solution B to mix gently for 10 min. Then, the functionalized polymer material (1 µg/µL, 10 µL) was added to the mixed solution to continue to mix for 10 min, to obtain final functionalized biopolymer material/protamine/molecular beacon nanoparticles. The synthesis process and action principle were shown in FIG. 1.

2. Synthesis of SHA/HA/PS/CHA Nanoparticles

Figure 2:
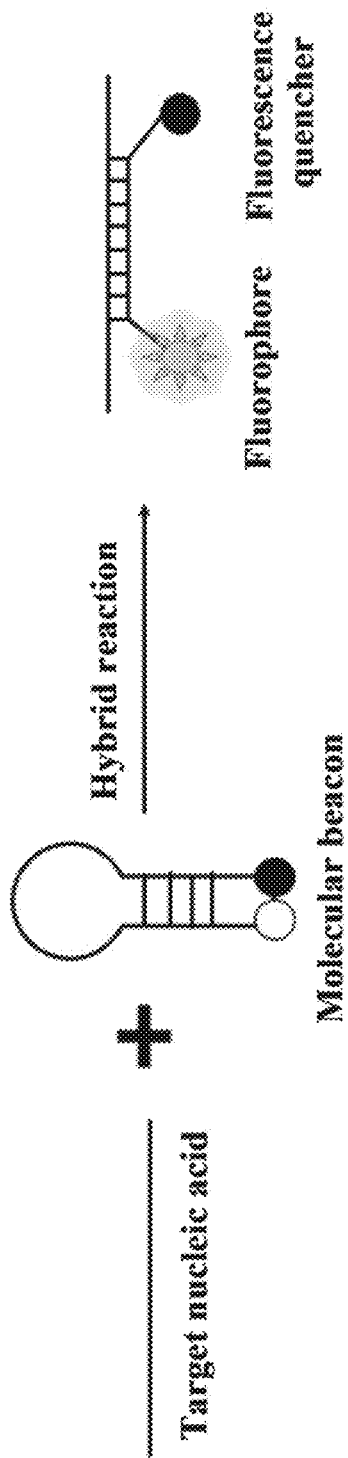
FIG. 2 is a diagram of an action principle of SHA/HA/PS/CHA in Example 1 according to the disclosure.

To further illustrate the synthesis process and experimental effects of the disclosure, an example is given for description. According to investigation and research, micro-RNA-21 is overexpressed in almost all tumor cells. Because the content of micro-RNA-21 is lower than that of messenger RNA in cells, it is difficult for common molecular beacons to achieve a relatively good detection effect on micro-RNA-21. CHA (a catalyzed hairpin assembly DNA reaction) uses a DNA or RNA strand to initiate two different hairpin molecular beacons to perform alternate recognition and undergo a hybridization reaction, to form an ultra-long double strand. This process does not require the participation of enzymes, so that the CHA has the advantages of low background signals and less false positive signals. The sensitivity of detecting nucleic acid is higher than that of detecting common molecular beacons, and therefore the CHA is suitable for detecting microRNA whose content is low in cells. Therefore, the sensitivity of detecting nucleic acid is higher than that of detecting common molecular beacons, and therefore the CHA is suitable for detecting microRNA whose content is low in cells. Therefore, to detect micro-RNA-21 in cells, an amplification system of the CHA encapsulated in the nanoparticles is selected. In addition, to better target the nanoparticles to tumor cells, an aptamer (SYL-3C) of epithelial cell adhesion molecules overexpressed by targeted cancer cells is modified on a polymer (sodium hyaluronate, HA) that composes the nanoparticles, and the final formed nanoparticles are SYL-3C functionalized sodium hyaluronate/sodium hyaluronate/protamine/CHA (SHA/HA/PS/CHA). The principle is shown in FIG. 2.

Figure 3:
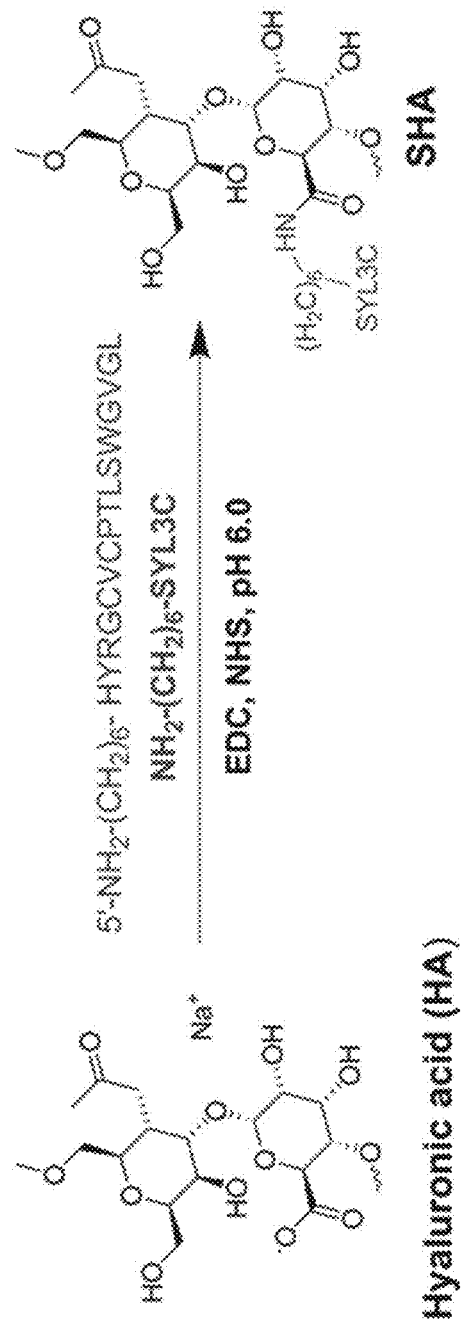
FIG. 3 shows a synthesis process of an SYL-3C aptamer-functionalized sodium hyaluronate material in Example 1 according to the disclosure.

The synthesis process of the SYL-3C functionalized sodium hyaluronate is shown in FIG. 3. The preparation process of the nanoparticles of the molecular beacon delivery system is as follows: (1) sodium hyaluronate (150 μg) was dissolved in a PBS buffer solution (pH=6.0, 1 mL), the mixed solution was activated with a catalyst EDC/HoBt (with a molar ratio of —COOH:EDC:HoBt=1:1.2:1.2) at room temperature for 1 h, an SYL-3C aptamer (150 μg) was then added to react at room temperature for 24 h, the product obtained after the reaction was placed in a dialysis bag (MWCO 10000) to be dialyzed with ultrapure water for 3 days, and the dialyzed product was freeze-dried, to finally obtain the SYL-3C functionalized sodium hyaluronate.

(2) A protamine solution (2 μg/μL, 15 μL) was mixed with deionized water (35 μL) to obtain a solution A with a total volume of 50 μL. A molecular beacon solution (a CHA solution) (H1: 50 nM, H2: 50 nM) was mixed with deionized water (40 μL) to obtain a solution B with a total volume of 50 μL. The solution A was dropwise added to the solution B to mix gently for 10 min. Then, the SYL-3C functionalized sodium hyaluronate (1 μg/μL, 10 μL) was added to the mixed solution to continue to mix for 10 min, to obtain the final SHA/HA/PS/CHA nanoparticles.

The SHA/HA/PS/CHA nanoparticles used in Examples 2 and 3 were prepared in this example.

Example 2

Characterization of SHA/HA/PS/CHA Nanoparticles
1. Measurement of the Particle Size, Potential, and Encapsulation Rate of SHA/HA/PS/CHA Nanoparticles Specific implementation method: an SHA/HA/PS/CHA nanoparticle solution prepared in Example 1 was diluted with deionized water to a total volume of 1 mL. The size and potential of the SHA/HA/PS/CHA nanoparticles in the deionized water were measured by using Zetasizer (Nano ZS, Malvern Instruments). Based on three independent tests, data was represented as mean±standard deviation (SD). To measure the encapsulation rate of the molecular beacon, the solution containing the SHA/HA/PS/CHA nanoparticles was centrifuged at a specific rotational speed (10000 rpm) at 4° C. for 1 h, and then the amount of unprecipitated free molecular beacons remaining in the supernatant was measured. The calculation of the encapsulation rate of the molecular beacons was based on the ratio of a precipitated beacon amount to a total feeding amount. The experimental result was shown in Table 1. It can be learned from the data in the table that the SHA/HA/PS/CHA nanoparticles have the hydrodynamic size less than 200 nm and are suitable for cells to take in. In addition, the encapsulation rate of the molecular beacons is 90% or more.

TABLE 1

| Sample name | Size (nm) | Potential (mV) | Molecular beacon encapsulation rate (%) |
|---|---|---|---|
| Protamine/molecular beacon Polymer | 140 ± 5 | 22.6 ± 0.1 | 90 |
| material/protamine/molecular beacon | 180 ± 8 | 11.4 ± 0.2 | 94 |
| SHA/HA/PS/CHA | 190 ± 9 | 10.8 ± 0.1 | 95 |

2. Morphology of SHA/HA/PS/CHA Nanoparticles Under a Transmission Electron Microscope (TEM)

Figure 4:
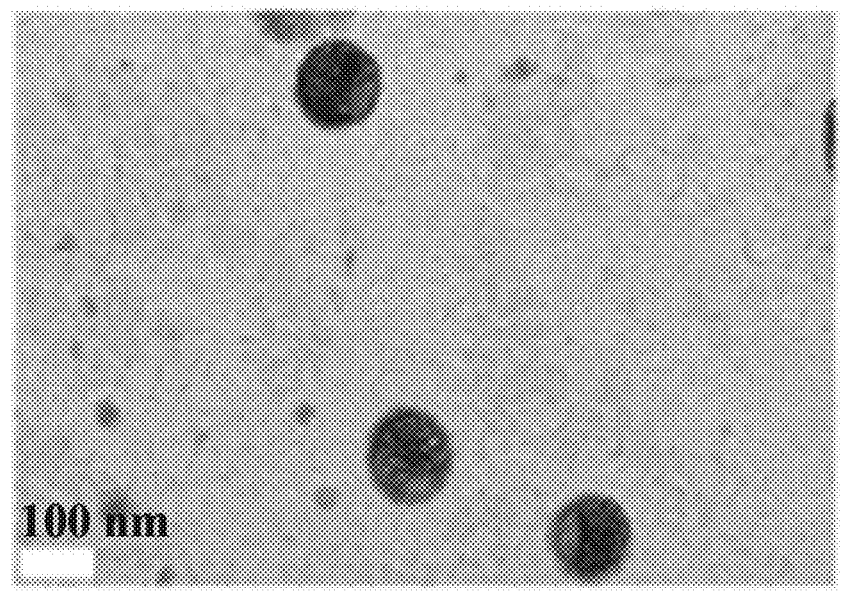
FIG. 4 is a characterization image of the morphology and particle size of SHA/HA/PS/CHA nanoparticles under a transmission electron microscope in Example 2 according to the disclosure.

Specific implementation method: an ultrathin carbon support film was infiltrated with a sample solution; and after the SHA/HA/PS/CHA nanoparticles were deposited, a small amount of phosphotungstic acid solution (0.001 mol/L) was added to perform infiltration and negative staining, and then the film was volatilized and dried at room temperature. Finally, the sample was observed by using a transmission electron microscope (JEM-2100). The experimental result was shown in FIG. 4. It can be learned from the figure that the SHA/HA/PS/CHA nanoparticles show uniformly dispersed spherical shapes.

3. Specificity of an Amplification System CHA

Figure 5:
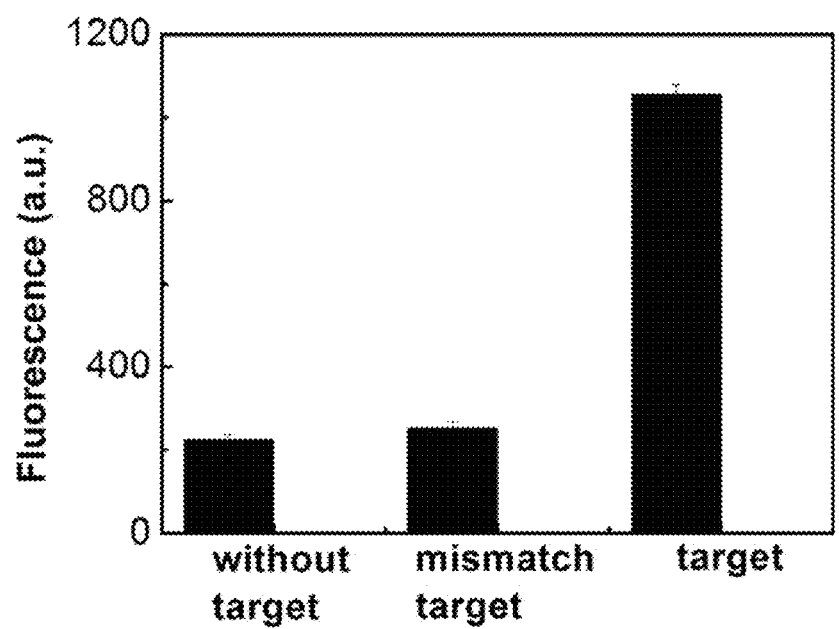
FIG. 5 is a graph showing fluorescence of CHA and two different nucleic acid molecules incubated for 4 h in Example 2 according to the disclosure.

Specific implementation method: in a HEPES buffer solution (pH=8, 10 mM), the SHA/HA/PS/CHA nanoparticles and nucleic acid molecules (including complementary targets miR-21 and mismatched mRNA) were hybridized. After a total of 4 hours of incubation, fluorescence was measured by using a spectrofluorophotometer (RF-5301PC, Japan). All experimental steps were repeated at least three times. Data was represented as mean±standard deviation (SD). The experimental result was shown in FIG. 5. It can be learned from the figure that, the bimolecular beacons of the amplification system bind with the complementary targets miR-21 to emit strong fluorescence, but fluorescence is hardly emitted when the bimolecular beacons bind with the mismatched nucleotides, showing that the bimolecular beacons of the amplification system have very good specificity, and show the result that greatly avoids false positives in cells.

4. Stability of SHA/HA/PS/CHA Nanoparticles

Figure 6:
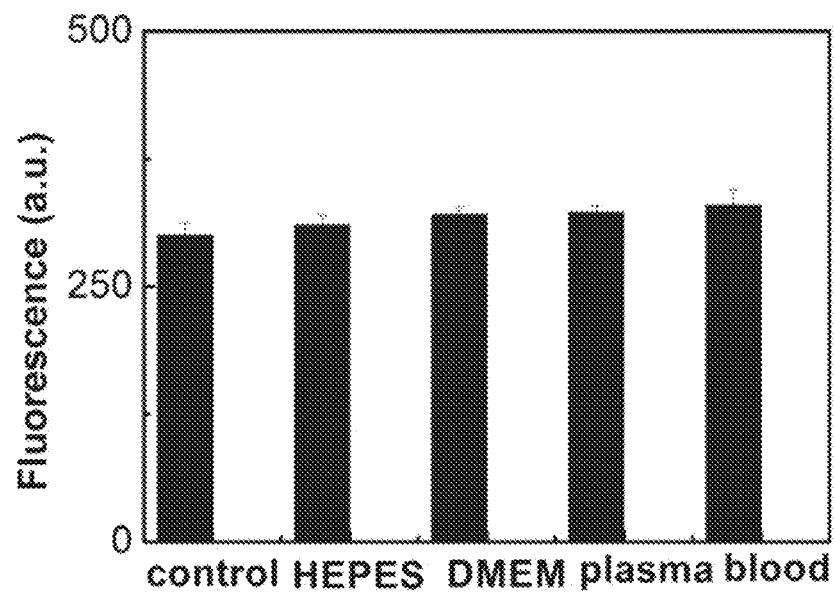
FIG. 6 is a graph showing fluorescence changes of SHA/HA/PS/CHA nanoparticles standing in different buffer solutions for 4 h in Example 2 according to the disclosure.

Specific implementation method: the SHA/HA/PS/CHA nanoparticles were added to 1 mL of HEPES buffer solution (pH=8, 10 mM), a DMEM medium, fetal bovine serum, and pig blood to stand for 4 h, and fluorescence was detected by using the spectrofluorophotometer (RF-5301PC, Japan). The experimental result was shown in FIG. 6. It can be learned from the figure that the SHA/HA/PS/CHA nanoparticles have very good stability in different solutions and can protect the CHA encapsulated inside from interference of impurities.

5. Biocompatibility of SHA/HA/PS/CHA Nanoparticles

Figure 7:
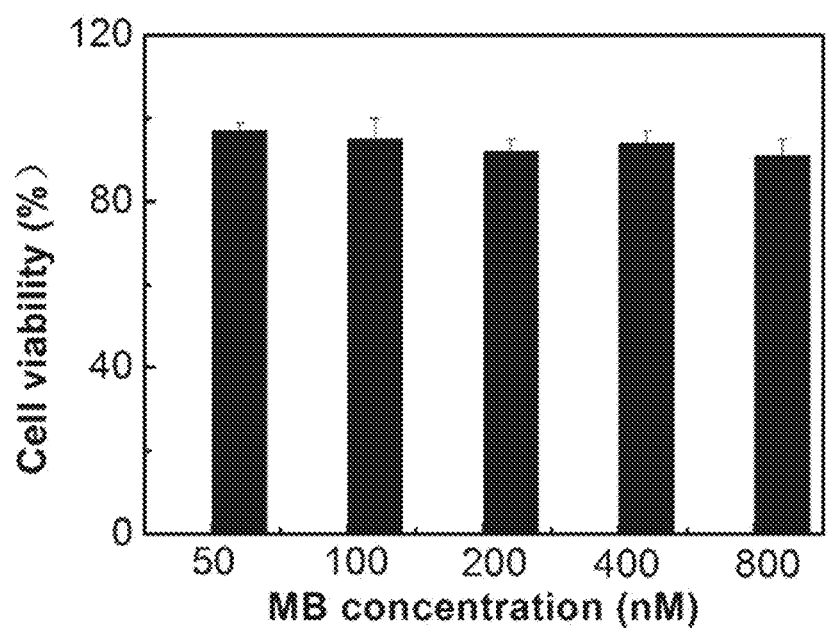
FIG. 7 is a graph showing viability of MCF-7 breast cancer cells after incubating SHA/HA/PS/CHA nanoparticles for 24 h in Example 2 according to the disclosure.

Specific implementation method: in vitro toxicity of the SHA/HA/PS/CHA nanoparticles to tumor cells was measured through the MTT assay. 104 MCF-7 breast cancer cells contained in the DMEM (100 μL) were inoculated into a 96-well plate to culture the cells for 24 h, and then 200 μL of nanoparticles were inoculated into the 96-well plate. After 4 hours of incubation at 37° C., DMSO was added to dissolve crystals generated by living cells. Finally, the absorbance value at 570 nm was measured by using a microplate reader. The experimental result was shown in FIG. 7. It can be learned from the figure that the cell viability of the SHA/HA/PS/CHA nanoparticles is 90% or more, showing that the materials have good biocompatibility.

Example 3

Figure 8:
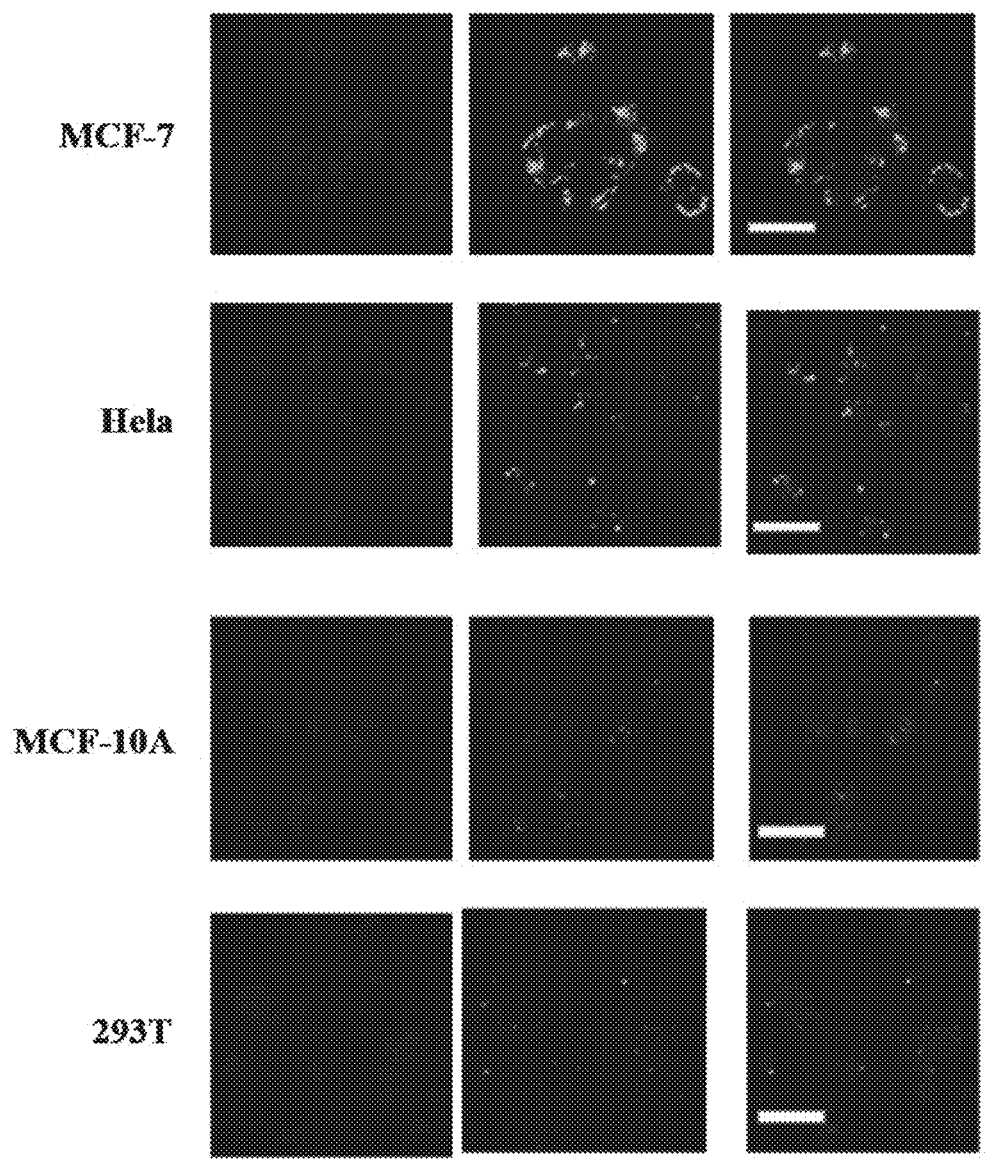
FIG. 8 is an image showing endocytosis of SHA/HA/PS/CHA nanoparticles in different cells (two tumor cells and two normal cells) detected in Example 3 according to the disclosure.

Target nucleic acid molecules in a sample were detected by using SHA/HA/PS/CHA nanoparticles.
1. Detection of SHA/HA/PS/CHA Nanoparticles at a Cell Line Level Specific implementation method: the cellular uptake and intracellular distribution of the SHA/HA/PS/CHA nanoparticles were mainly measured by confocal laser scanning microscopy (CLSM). First, tumor cells (MCF-7, HeLa) and normal cells (MCF-10A, 293T) were inoculated into a 35 mm confocal dish to culture the cells for 24 h, and then 1 mL of SHA/HA/PS/CHA nanoparticle solution was added to the confocal dish to be incubated with the cells for a total of 4 h. Then, the nucleus was stained by using Hoechest 33342, and finally the cells were observed by CLSM (PerkinElmer MltraVIEW VoX). The experimental result was shown in FIG. 8. It can be learned from the figure that the light emitted by the two cancer cells (MCF-7, HeLa) is much stronger than that of the two normal cells (MCF-10A, 293T), and this is because the content of microRNA-21 expressed in the cancer cells is much higher than that in the normal cells. The result shows that the synthesized SHA/HA/PS/CHA nanoparticles can distinguish cancer cells from normal cells.

2. Detection of SHA/HA/PS/CHA Nanoparticles at a Simulated Blood Level

Figure 9:
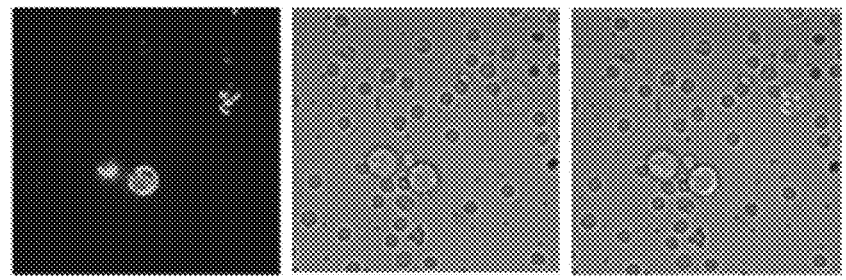
FIG. 9 is an image showing tumor cells endocytosing SHA/HA/PS/CHA nanoparticles in a simulated blood environment detected in Example 3 according to the disclosure.

Specific implementation method: 1000 MCF-7 cells were mixed into 2 mL of healthy human blood to stand for 2 h. Then, 1 mL of SHA/HA/PS/CHA nanoparticle solution was added to the blood to be incubated for 4 h. In this case, the blood was added to a 15 mL lymphocyte separation tube and centrifuged at a rotational speed of 800 g per minute for 20 min, a PBMC layer was taken and added to a confocal dish, the nucleus was stained by using Hoechest 33342, and then the cells were observed by CLSM. The experimental result was shown in FIG. 9. The cancer cells emit strong fluorescence, but the red blood cells and white blood cells hardly emit fluorescence, showing that the SHA/HA/PS/CHA nanoparticles can accurately target the cancer cells in a complex blood environment, and microRNA-21 in the cancer cells is detected.

3. Detection of SHA/HA/PS/CHA Nanoparticles in Real Patient Blood

Figure 10:
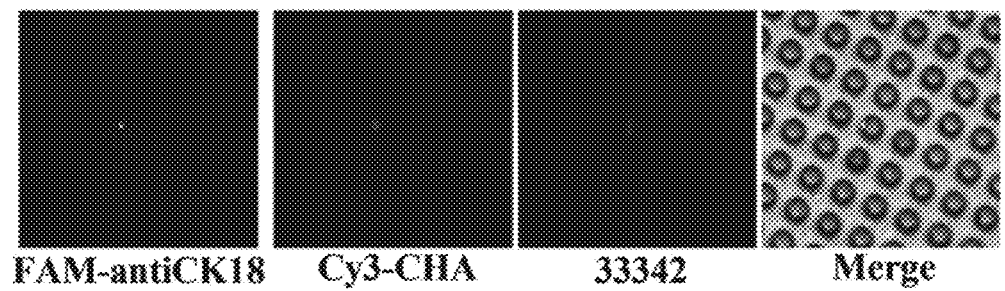
FIG. 10 is an image showing circulating tumor cells endocytosing SHA/HA/PS/CHA nanoparticles in a blood environment of real patients detected in Example 3 according to the disclosure.

Specific implementation method: 2 mL of cancer patient blood was taken into an EDTA anticoagulant tube, 1 mL of the SHA/HA/PS/CHA nanoparticle solution was added to the blood to be incubated for 6 h, the blood was placed on a filter membrane with a diameter of 70 μm for filtration, the filter membrane was collected in a confocal dish and stained with the CK18 antibody, the nucleus was stained by using Hoechest 33342, and then the cells were observed by CLSM. The experimental result was shown in FIG. 10. Three lights of circulating tumor cells overlap together, showing that there is no need to enrich the circulating tumor cells, and the SHA/HA/PS/CHA nanoparticles can directly and efficiently target the inside of the tumor cells in the cancer patient blood, and microRNA-21 in the cells is detected. The result provides a basis for early tumor detection, medication guidance, and late monitoring.

It will be obvious to those skilled in the art that changes and modifications may be made, and therefore, the aim in the appended claims is to cover all such changes and modifications.

What is claimed is:

1. A preparation method of a molecular beacon delivery system for directly detecting circulating tumor cells in blood, wherein the molecular beacon delivery system comprises nanoparticles self-assembled by a polymer material, protamine, and a molecular beacon, and the method consists of:
   (1) aptamer-functionalizing or polypeptide-functionalizing the polymer material to obtain a functionalized polymer material, wherein the polymer material comprises any one of aptamer-functionalized hyaluronic acid, aptamer-functionalized sodium alginate, polypeptide-functionalized sodium alginate, aptamer-functionalized heparin sodium, and polypeptide-functionalized heparin sodium;
   (2) adding only deionized water to a protamine solution to form a solution A, adding only deionized water to a molecular beacon solution to form a solution B, and dropwise adding the solution A to the solution B and mixing evenly; and
   (3) adding the functionalized polymer material obtained in (1) to the mixed solution obtained in (2), and continually mixing evenly, to obtain the molecular beacon delivery system;
   wherein in (3), after the functionalized polymer material is added, a mass ratio of the protamine to the molecular beacon to the functionalized polymer material in the mixed solution is 30:1-2:5-15, and a concentration of the protamine is 0.3 μg/μL;
   wherein in (1), the functionalized polymer material is prepared with operations in one of I or II:
   I. dissolving the polymer material in a PBS buffer solution, adding a catalyst EDC/HoBt for activation at 25° C., and then adding aminated aptamer or polypeptide and reacting at 25° C.; and placing the product obtained after an amidation reaction in a dialysis bag for dialysis, and freeze-drying the dialyzed product, to obtain the functionalized polymer material; or
   II. dissolving aptamer or polypeptide in a PBS buffer solution, adding a catalyst EDC/HoBt for activation at 25° C., and then adding the polymer material and reacting at 25° C.; and placing the product obtained after an amidation reaction in a dialysis bag for dialysis, and freeze-drying the dialyzed product, to obtain the functionalized polymer material,
   wherein in I and II, after the catalyst EDC/HoBt is added, a molar ratio of —COOH to EDC to HoBt in the solution is 1:1.2:1.2, and a molar ratio of the polymer material to the aptamer or the polypeptide is 10:1.

2. The method of claim 1, wherein the molecular beacon comprises any one of a common molecular beacon, a locked molecular beacon, a stemless molecular beacon, a fluorescence transfer molecular beacon, catalyzed hairpin assembly (CHA), and hybridization chain reaction (HCR).

3. The method of claim 1, wherein for the molecular beacon, a 5' end of the molecular beacon is marked with a fluorophore, and a 3' end of the molecular beacon is marked with a fluorescence quencher.

* * * * *